United States Patent
Morgan et al.

(10) Patent No.: US 6,850,798 B2
(45) Date of Patent: Feb. 1, 2005

(54) METHOD AND APPARATUS FOR MEASURING BODY FAT IN ANIMALS

(75) Inventors: Blair P. Morgan, Ballwin, MO (US); Nathan Trone, Milwaukie, OR (US); Benjamin T. Richardson, Vancourver, WA (US); Carl D. Sorensen, Provo, UT (US); Jason T. Smith, Cambridge, MA (US); James A. LeFevre, Draper, UT (US); Jeremy B. Clark, Albany, GA (US); Tyson J. Baker, Salt Lake City, UT (US); Samuel B. Sheppard, Callaway, MD (US)

(73) Assignee: Nestec, Ltd., Vevey (CH)

( * ) Notice: Subject to any disclaimer, the term of this patent is extended or adjusted under 35 U.S.C. 154(b) by 0 days.

(21) Appl. No.: 10/266,395

(22) Filed: Oct. 8, 2002

(65) Prior Publication Data

US 2004/0068379 A1 Apr. 8, 2004

(51) Int. Cl.[7] ................................................ A61B 5/05

(52) U.S. Cl. .................... 600/547; 600/372; 119/174

(58) Field of Search ................................ 600/547, 372, 600/382, 393; 119/174

(56) References Cited

U.S. PATENT DOCUMENTS 6,088,615 A * 7/2000 Masuo ........................ 600/547
6,490,481 B1 * 12/2002 Komatsu et al. ............ 600/547
6,567,692 B1 * 5/2003 Kohashi et al. ............. 600/547

OTHER PUBLICATIONS

Burkholder, Wm. J., *Body composition of dogs determined by carcass composition analysis, deuterium oxide dilution, subjective and objective morphometry, and bioelectrical impedance*, Abstract, 168–209 (Date Unknown).

Burkholder, Wm. J., *Precision and practicality of methods assessing body composition of dogs and cats*, Texas A & M University, 1–15 (Date Unknown).

Hoffer, et al., *Correlation of whole–body impedance with total body water volume*, Journal of Applied Physiology, 27:531–534 (1969).

Kotler, et al., *Prediction of body cell mass, fat–free mass, and total body water with bioelectrical impedance analysis: effects of race, sex, and disease*, American Journal of Clinical Nutrition, 64:489–497 (1996).

Sedensky, et al., *Electrical impedance derived measurement of total body water and extracellular fluid volume in healthy mongrel dogs*, Abstract, 7th Annual Michigan Cardiovascular Research Forum, (1997).

* cited by examiner

Primary Examiner—Charles Marmor
(74) Attorney, Agent, or Firm—Sanjay Agrawal, Esq.; Armstrong Teasdale LLP

(57) ABSTRACT

A method for measuring a body composition measure of an animal includes steps of measuring a first electrical impedance between a front foot pad of the animal and a rear foot pad of the animal; measuring a second electrical impedance between two front foot pads of the animal in parallel with one another and two rear foot pads of the animal in parallel with one another; and utilizing the first electrical impedance, the second electrical impedance, and a regression relationship to determine the body composition measure of the animal.

32 Claims, 17 Drawing Sheets

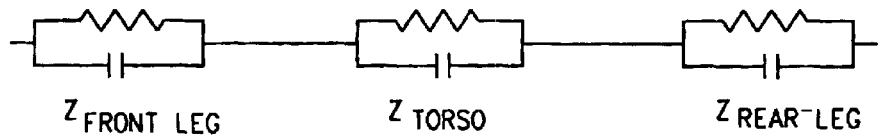
$Z_{FRONT\ LEG}$   $Z_{TORSO}$   $Z_{REAR\ LEG}$
F I G . 7
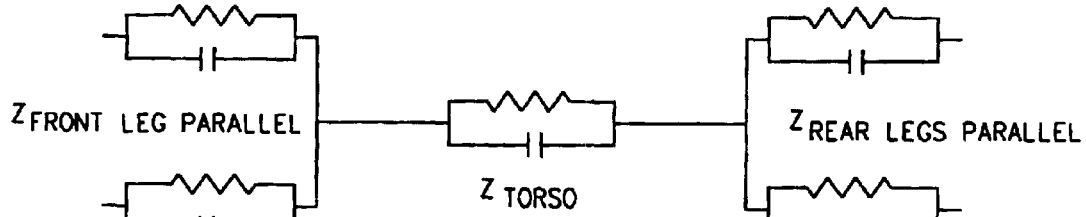
$Z_{FRONT\ LEG\ PARALLEL}$   $Z_{TORSO}$   $Z_{REAR\ LEGS\ PARALLEL}$
F I G . 8
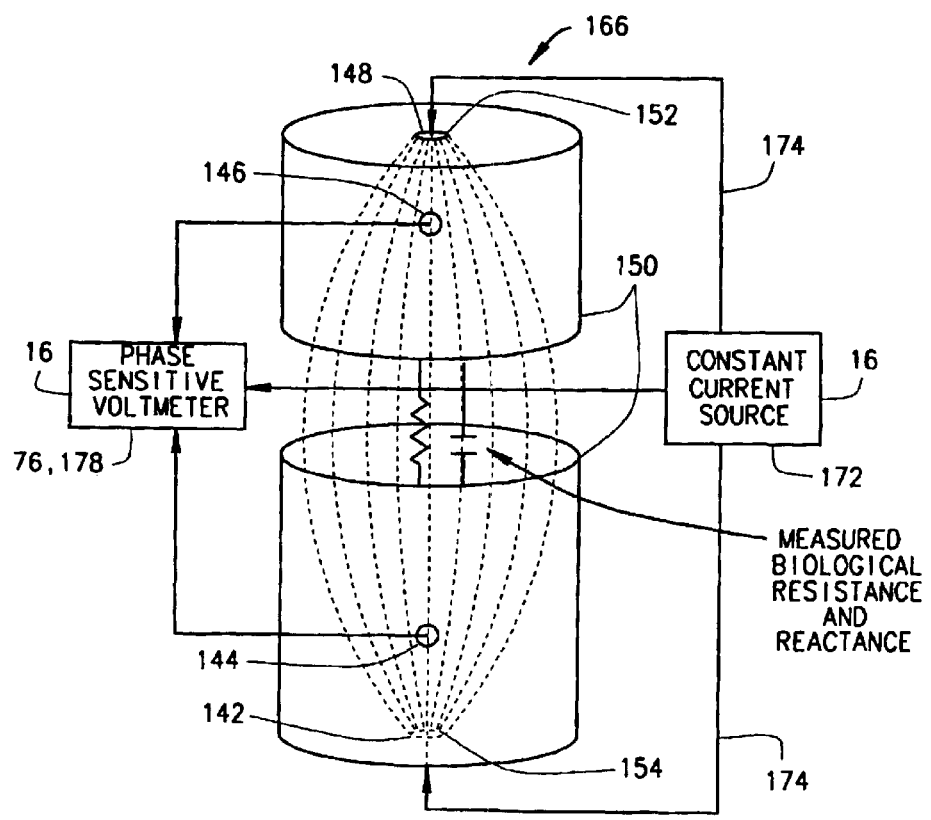
F I G . 9 PRIOR ART

| % FAT=-27.2 - 2.16 WEIGHT + 2.85 ABD GIRTH + 0.0326 BODY RESISTANCE -67.7 AB/THRX | | | | |
|---|---|---|---|---|
| PREDICTOR | COEF | SE COEF | T | P |
| CONSTANT | -27.190 | 4.814 | -5.65 | 0.000 |
| WEIGHT | -2.1622 | 0.3355 | -6.45 | 0.000 |
| ABD GIRT | 2.8465 | 0.3112 | 9.15 | 0.000 |
| BODY RES | 0.032616 | 0.007355 | 4.43 | 0.000 |
| AB/THRX | -67.651 | 8.512 | -7.95 | 0.000 |
| S = 3.704  R-SQ = 87.4%  R-SQ(ADJ) = 85.8% | | | | |

| DOG ID | BREED | SEX | WEIGHT KILO-GRAMS | LENGTH (cm) | THORAX GIRTH (cm) | ABDOMEN GIRTH (cm) |
|---|---|---|---|---|---|---|
| R347 | SCH | F | 7.3 | 56 | 45 | 39 |
| K102 | SCH | F | 8.25 | 62 | 44 | 40 |
| P307 | SCH | F | 7.95 | 57 | 43 | 39 |
| P306 | SCH | F | 6.8 | 57 | 43 | 34 |
| Q116 | SCH | M | 7.7 | 63 | 43 | 37 |
| K262 | SCH | M | 9.7 | 65 | 45 | 39 |
| P717 | SCH | M | 7.6 | 57 | 44 | 36 |
| P351 | LR | F | 36.4 | 96 | 77 | 73 |
| R102 | LR | F | 37.9 | 92 | 81 | 71 |
| P75 | LR | F | 23.55 | 99 | 64 | 49 |
| P292 | LR | F | 23.6 | 88 | 67 | 47 |
| U14 | LR | F | 28.5 | 90 | 72 | 50 |
| P67 | LR | M | 37.9 | 104 | 74 | 67 |
| P287 | LR | M | 29 | 93 | 72.5 | 58 |
| N373 | S | F | 18.95 | 96 | 60 | 44 |
| M287 | S | F | 23.1 | 100 | 66 | 55 |
| N519 | S | F | 19.4 | 97 | 42.5 | 58.5 |
| N523 | S | F | 16.3 | 91 | 40.5 | 57.5 |
| M400 | S | F | 22.3 | 95 | 68 | 53 |
| M649 | S | F | 23.9 | 104 | 60 | 51 |
| M5 | S | F | 19.9 | 99 | 60 | 48 |
| M744 | S | F | 16.25 | 93 | 58 | 41.5 |
| M22 | S | F | 15.15 | 94 | 58 | 41 |
| M365 | S | F | 21.25 | 93 | 65 | 51 |
| M743 | S | F | 17.3 | 91 | 58 | 42 |
| M47 | S | F | 20.1 | 91 | 57 | 48 |
| M286 | S | F | 23.55 | 96 | 63 | 56 |
| L681 | S | F | 21.6 | 96 | 66 | 52 |
| L688 | S | F | 18.2 | 90 | 61.5 | 42 |
| M397 | S | F | 24.7 | 91 | 70 | 55 |
| M285 | S | F | 20.5 | 95 | 60 | 48 |
| N522 | S | F | 16.05 | 91 | 60 | 37 |
| M364 | S | M | 21.7 | 96 | 66 | 46 |
| M573 | S | M | 19.55 | 99 | 61 | 44 |
| M392 | S | M | 23.3 | 107 | 69 | 51 |
| O370 | S | M | 24.85 | 102 | 70 | 51 |

FIG. 11

| DOG ID | BCS SCORE | HEIGHT (FLOOR TO MIDDLE OF SCAPULAS) cm | LENGTH (MIDDLE OF SCAPULAS TO BASE OF TAIL) cm | LENGTH (BASE OF NECK TO BASE OF TAIL) cm | AB/THORX |
|---|---|---|---|---|---|
| R347 | 6 | 33 | 28 | 31 | 0.867 |
| K102 | 6 | 37 | 33 | 34.5 | 0.909 |
| P307 | 5 | 36 | 31 | 34 | 0.907 |
| P306 | 5 | 40 | 32 | 35 | 0.791 |
| Q116 | 6 | 25.5 | 37 | 38 | 0.860 |
| K262 | 6 | 43 | 36 | 38 | 0.867 |
| P717 | 5 | 36.5 | 29 | 32 | 0.818 |
| P351 | 9 | 56 | 51 | 53 | 0.948 |
| R102 | 9 | 56 | 49 | 52 | 0.877 |
| P75 | 5 | 58 | 50 | 53 | 0.766 |
| P292 | 6 | 60 | 48 | 52 | 0.701 |
| U14 | 4 | 64 | 49 | 53 | 0.694 |
| P67 | 8 | 63 | 57 | 63 | 0.905 |
| P287 | 5 | 62 | 56 | 59 | 0.800 |
| N373 | 4 | 56 | 48 | 51 | 0.733 |
| M287 | 6 | 52 | 46 | 49 | 0.833 |
| N519 | 4 | 54 | 48 | 54 | 1.376 |
| N523 | 4 | 52 | 50 | 54 | 1.420 |
| M400 | 6 | 55 | 51 | 54 | 0.779 |
| M649 | 6 | 63 | 55 | 64 | 0.850 |
| M5 | 5 | 53 | 54 | 60 | 0.800 |
| M744 | 5 | 48 | 47 | 54 | 0.716 |
| M22 | 5 | 51 | 48 | 55 | 0.707 |
| M365 | 7 | 52 | 47 | 52 | 0.785 |
| M743 | 5 | 48 | 45 | 52 | 0.724 |
| M47 | 5 | 63 | 59 | 63 | 0.842 |
| M286 | 6 | 47 | 46 | 53 | 0.889 |
| L681 | 6 | 47 | 45 | 58 | 0.788 |
| L688 | 5 | 56 | 48 | 55 | 0.683 |
| M397 | 7 | 47 | 51 | 55 | 0.786 |
| M285 | 6 | 49 | 54 | 60 | 0.800 |
| N522 | 4 | 49 | 35 | 51 | 0.617 |
| M364 | 5 | 56 | 39 | 54 | 0.697 |
| M573 | 5 | 53 | 45 | 53 | 0.721 |
| M392 | 5 | 54 | 53 | 57 | 0.739 |
| O370 | 5 | 64 | 54 | 56 | 0.729 |

FIG. 12

| DOG ID | IMPEDANCE WITH 4 FEET ON THE MAT (OHMS) | | | | | |
|---|---|---|---|---|---|---|
| | REP 1 | | REP 2 | | REP 3 | |
| | RES | REACT | RES | REACT | RES | REACT |
| R347 | 874 | 115 | 864 | 110 | 873 | 134 |
| K102 | 881 | 149 | 872 | 146 | 862 | 143 |
| P307 | 832 | 116 | 838 | 117 | 839 | 117 |
| P306 | 1041 | 184 | 1040 | 184 | 1031 | 180 |
| Q116 | 857 | 109 | 862 | 110 | 860 | 108 |
| K262 | 909 | 131 | 914 | 132 | 908 | 130 |
| P717 | 940 | 160 | 955 | 158 | 976 | 150 |
| P351 | 692 | 88 | 685 | 86 | 678 | 85 |
| R102 | 689 | 148 | 655 | 116 | 651 | 113 |
| P75 | 698 | 87 | 695 | 87 | 695 | 87 |
| P292 | 758 | 98 | 765 | 99 | 772 | 99 |
| U14 | 677 | 80 | 685 | 80 | 682 | 80 |
| P67 | 704 | 112 | 605 | 72 | 605 | 72 |
| P287 | 736 | 96 | 735 | 94 | 734 | 94 |
| N373 | 1018 | 170 | 996 | 162 | 989 | 156 |
| M287 | 814 | 101 | 818 | 100 | 819 | 100 |
| N519 | 836 | 104 | 840 | 111 | 841 | 103 |
| N523 | 929 | 135 | 921 | 127 | 914 | 120 |
| M400 | 905 | 114 | 916 | 106 | 888 | 113 |
| M649 | 887 | 117 | 865 | 124 | 877 | 105 |
| M5 | 1069 | 156 | 1068 | 152 | 1070 | 157 |
| M744 | 1042 | 139 | 1043 | 137 | 1080 | 137 |
| M22 | 1124 | 161 | 1153 | 164 | 1161 | 160 |
| M365 | 994 | 133 | 981 | 129 | 971 | 127 |
| M743 | 1060 | 163 | 1052 | 160 | 1045 | 168 |
| M47 | 1099 | 172 | 1092 | 160 | 1070 | 152 |
| M286 | 909 | 117 | 928 | 118 | 880 | 119 |
| L681 | 1021 | 166 | 1009 | 155 | 971 | 142 |
| L688 | 1094 | 183 | 1090 | 170 | 1038 | 158 |
| M397 | 982 | 194 | 962 | 168 | 940 | 134 |
| M285 | 981 | 155 | 945 | 127 | 932 | 135 |
| N522 | 907 | 127 | 915 | 126 | 932 | 125 |
| M364 | 785 | 112 | 775 | 106 | 767 | 100 |
| M573 | 971 | 153 | 934 | 140 | 935 | 135 |
| M392 | 1033 | 164 | 1000 | 131 | 977 | 125 |
| O370 | 975 | 220 | 972 | 131 | 950 | 133 |

FIG. 13

| DOG ID | IMPEDANCE WITH 2 FEET ON THE MAT (OHMS) | | | | | |
|---|---|---|---|---|---|---|
| | REP 1 | | REP 2 | | REP 3 | |
| | RES | REACT | RES | REACT | RES | REACT |
| R347 | 1594 | 252 | 1593 | 247 | 1611 | 251 |
| K102 | 1661 | 299 | 1685 | 306 | 1666 | 304 |
| P307 | 1536 | 235 | 1536 | 235 | 1538 | 235 |
| P306 | 1875 | 348 | 1854 | 350 | 1853 | 333 |
| Q116 | 1665 | 255 | 1662 | 242 | 1630 | 247 |
| K262 | 1665 | 163 | 1693 | 272 | 1650 | 260 |
| P717 | 1741 | 314 | 1768 | 310 | 1748 | 300 |
| P351 | 1173 | 178 | 1154 | 177 | 1148 | 175 |
| R102 | 1106 | 169 | 1111 | 163 | 1114 | 164 |
| P75 | 1308 | 184 | 1308 | 183 | 1252 | 171 |
| P292 | 1201 | 172 | 1205 | 175 | 1218 | 173 |
| U14 | 1341 | 170 | 1278 | 170 | 1280 | 168 |
| P67 | 1122 | 161 | 1097 | 158 | 1095 | 158 |
| P287 | 1447 | 223 | 1439 | 224 | 1468 | 218 |
| N373 | 1738 | 309 | 1730 | 307 | 1709 | 323 |
| M287 | 1552 | 222 | 1514 | 221 | 1555 | 223 |
| N519 | 1499 | 219 | 1583 | 228 | 1575 | 223 |
| N523 | 1557 | 244 | 1638 | 255 | 1628 | 247 |
| M400 | 1602 | 232 | 1576 | 238 | 1602 | 226 |
| M649 | 1533 | 210 | 1572 | 208 | 1533 | 204 |
| M5 | 1946 | 383 | 1886 | 335 | 1863 | 318 |
| M744 | 1905 | 332 | 1899 | 298 | 1886 | 330 |
| M22 | 1889 | 344 | 1935 | 338 | 1958 | 331 |
| M365 | 1752 | 320 | 1691 | 360 | 1775 | 323 |
| M743 | 1790 | 308 | 1790 | 303 | 1778 | 293 |
| M47 | 1841 | 345 | 1807 | 335 | 1734 | 311 |
| M286 | 1625 | 272 | 1636 | 270 | 1674 | 268 |
| L681 | 1925 | 354 | 1660 | 283 | 1600 | 264 |
| L688 | 1950 | 388 | 1888 | 366 | 1784 | 336 |
| M397 | 1847 | 351 | 1664 | 314 | 1660 | 306 |
| M285 | 1713 | 283 | 1617 | 258 | 1596 | 252 |
| N522 | 1732 | 287 | 1711 | 283 | 1677 | 261 |
| M364 | 1375 | 208 | 1353 | 203 | 1360 | 201 |
| M573 | 1632 | 290 | 1620 | 288 | 1645 | 290 |
| M392 | 1930 | 425 | 1910 | 346 | 1922 | 366 |
| O370 | 1679 | 247 | 1658 | 248 | 1711 | 258 |

FIG. 14

| DOG ID | $R_4$, AVE. | $R_2$, AVE. | $R_{TORSO}$ CORRECTED | $C_4$, AVE. | $C_2$, AVE. | $C_{TORSO}$ CORRECTED | R PARALLEL |
|---|---|---|---|---|---|---|---|
| R347 | 870 | 1599 | 141 | 119.7 | 250.0 | -10.7 | 141.3 |
| K102 | 872 | 1671 | 73 | 146.0 | 303.0 | -11.0 | 72.5 |
| P307 | 836 | 1537 | 136 | 116.7 | 235.0 | -1.7 | 136.0 |
| P306 | 1037 | 1861 | 214 | 182.7 | 343.7 | 21.7 | 214.1 |
| Q116 | 860 | 1652 | 67 | 109.0 | 248.0 | -30.0 | 66.6 |
| K262 | 910 | 1669 | 151 | 131.0 | 231.7 | 30.3 | 151.5 |
| P717 | 957 | 1752 | 162 | 156.0 | 308.0 | 4.0 | 161.7 |
| P351 | 685 | 1158 | 212 | 86.3 | 176.7 | -4.0 | 211.6 |
| R102 | 665 | 1110 | 220 | 125.7 | 165.3 | 86.0 | 220.1 |
| P75 | 696 | 1289 | 103 | 87.0 | 179.3 | -5.3 | 102.6 |
| P292 | 765 | 1208 | 322 | 98.7 | 173.3 | 24.0 | 322.1 |
| U14 | 681 | 1300 | 63 | 80.0 | 169.3 | -9.3 | 62.9 |
| P67 | 638 | 1105 | 171 | 85.3 | 159.0 | 11.7 | 171.4 |
| P287 | 735 | 1451 | 19 | 94.7 | 221.7 | -32.3 | 16.9 |
| N373 | 1001 | 1726 | 276 | 162.7 | 313.0 | 12.3 | 276.4 |
| M287 | 817 | 1540 | 94 | 100.3 | 222.0 | -21.3 | 93.4 |
| N519 | 839 | 1552 | 126 | 106.0 | 223.3 | -11.3 | 125.6 |
| N523 | 921 | 1608 | 235 | 127.3 | 248.7 | 6.0 | 235.0 |
| M400 | 903 | 1593 | 213 | 111.0 | 232.0 | -10.0 | 212.6 |
| M649 | 876 | 1546 | 207 | 115.3 | 207.3 | 23.3 | 206.8 |
| M5 | 1069 | 1898 | 240 | 155.0 | 345.3 | -35.3 | 239.5 |
| M744 | 1055 | 1897 | 213 | 137.7 | 320.0 | -44.7 | 213.1 |
| M22 | 1146 | 1927 | 365 | 161.7 | 337.7 | -14.3 | 364.6 |
| M365 | 982 | 1739 | 225 | 129.7 | 334.3 | -75.0 | 224.3 |
| M743 | 1052 | 1786 | 319 | 163.7 | 301.3 | 26.0 | 318.7 |
| M47 | 1087 | 1794 | 380 | 161.3 | 330.3 | -7.7 | 380.0 |
| M286 | 906 | 1645 | 166 | 118.0 | 270.0 | -34.0 | 166.1 |
| L681 | 1000 | 1728 | 272 | 154.3 | 300.3 | 8.3 | 272.4 |
| L688 | 1074 | 1874 | 274 | 170.3 | 363.3 | -22.7 | 273.9 |
| M397 | 961 | 1724 | 199 | 165.3 | 323.7 | 7.0 | 199.0 |
| M285 | 953 | 1642 | 263 | 139.0 | 264.3 | 13.7 | 263.4 |
| N522 | 918 | 1707 | 129 | 126.0 | 277.0 | -25.0 | 129.1 |
| M364 | 776 | 1363 | 189 | 106.0 | 204.0 | 8.0 | 188.7 |
| M573 | 947 | 1632 | 261 | 142.7 | 289.3 | -4.0 | 261.0 |
| M392 | 1003 | 1921 | 86 | 140.0 | 379.0 | -99.0 | 84.8 |
| O370 | 966 | 1683 | 249 | 161.3 | 251.0 | 71.7 | 249.0 |

FIG. 15

| DOG ID | % FAT (DEXA) | REGRESSION PREDICTED % BF (FROM BIA EQUATION) |
|---|---|---|
| R347 | 6.3 | 14.12 |
| K102 | 7.7 | 9.80 |
| P307 | 12.3 | 9.81 |
| P306 | 13.7 | 8.46 |
| Q116 | 6.3 | 5.55 |
| K262 | 11.6 | 9.26 |
| P717 | 9.7 | 8.86 |
| P351 | 42.7 | 44.94 |
| R102 | 42.6 | 41.11 |
| P75 | 7 | 13.10 |
| P292 | 15.6 | 18.78 |
| U14 | 5.1 | 8.78 |
| P67 | 26.1 | 26.18 |
| P287 | 23.9 | 21.91 |
| N373 | 12.6 | 16.63 |
| M287 | 27.4 | 26.29 |
| N519 | 8.1 | 8.53 |
| N523 | 11.8 | 13.01 |
| M400 | 29.9 | 29.85 |
| M649 | 22.5 | 15.72 |
| M5 | 19.6 | 20.27 |
| M744 | 11.6 | 14.19 |
| M22 | 17.7 | 20.96 |
| M365 | 28.8 | 26.46 |
| M743 | 17 | 16.50 |
| M47 | 21.1 | 21.56 |
| M286 | 27.8 | 26.78 |
| L681 | 26.6 | 29.88 |
| L688 | 14.5 | 15.89 |
| M397 | 36.8 | 29.49 |
| M285 | 18.7 | 19.74 |
| N522 | 9 | 6.05 |
| M364 | 19.4 | 15.99 |
| M573 | 21.1 | 15.65 |
| M392 | 14.6 | 20.59 |
| O370 | 21.3 | 23.26 |

FIG. 16

% FAT=−39.4 − 1.81 WEIGHT + 2.67 ABD GIRTH − 62.9 AB/THRX + 0.0177 R4

| PREDICTOR | COEF | SE COEF | T | P |
|---|---|---|---|---|
| CONSTANT | −39.358 | 9.397 | −4.19 | 0.000 |
| WEIGHT | −1.8132 | 0.3929 | −4.61 | 0.000 |
| ABD GIRT | 2.6746 | 0.3578 | 7.47 | 0.000 |
| AB/THRX | −62.892 | 9.953 | −6.32 | 0.000 |
| R4 | 0.017743 | 0.006622 | 2.68 | 0.012 |

S = 4.267  R-SQ = 83.3%  R-SQ(ADJ) = 81.1%

% FAT=−31.2 − 1.85 WEIGHT + 2.67 ABD GIRTH − 64.2 AB/THRX + 0.00621 R2

| PREDICTOR | COEF | SE COEF | T | P |
|---|---|---|---|---|
| CONSTANT | −31.24 | 10.98 | −2.85 | 0.008 |
| WEIGHT | −1.8511 | 0.4335 | −4.27 | 0.000 |
| ABD GIRT | 2.6696 | 0.3873 | 6.89 | 0.000 |
| AB/THRX | −64.24 | 10.82 | −5.94 | 0.000 |
| R2 | 0.006213 | 0.004506 | 1.38 | 0.178 |

S = 4.597  R-SQ = 80.6%  R-SQ(ADJ) = 78.1%

% FAT=−26.3 + 0.00063 RHO + 0.0304 BODY RESISTANCE − 2.14 WEIGHT + 2.81 ABD GIRTH − 67.2 AB/THRX

| PREDICTOR | COEF | SE COEF | T | P |
|---|---|---|---|---|
| CONSTANT | −26.268 | 8.874 | −2.96 | 0.006 |
| RHO | 0.000634 | 0.005093 | 0.12 | 0.902 |
| BODY RES | 0.03043 | 0.01909 | 1.59 | 0.121 |
| WEIGHT | −2.1365 | 0.3984 | −5.36 | 0.000 |
| ABD GIRT | 2.8085 | 0.4396 | 6.39 | 0.000 |
| AB/THRX | −67.238 | 9.263 | −7.26 | 0.000 |

S = 3.765  R-SQ = 87.4%  R-SQ(ADJ) = 85.3%

FIG. 20

| % FAT=−3.10 + 0.0266 BODY RESISTANCE + 0.823 WEIGHT |||||
|---|---|---|---|---|
| PREDICTOR | COEF | SE COEF | T | P |
| CONSTANT | −3.099 | 3.983 | −0.78 | 0.442 |
| BODY RES | 0.02660 | 0.01351 | 1.97 | 0.057 |
| WEIGHT | 0.8235 | 0.1441 | 5.71 | 0.000 |
| S = 6.909  R-SQ = 53.3%  R-SQ(ADJ) = 50.5% |||||

| % FAT= 9.95 + 0.0370 BODY RESISTANCE + 1.18 WEIGHT − 0.478 LENGTH 1 |||||
|---|---|---|---|---|
| PREDICTOR | COEF | SE COEF | T | P |
| CONSTANT | 9.953 | 7.452 | 1.34 | 0.191 |
| BODY RES | 0.03698 | 0.01388 | 2.66 | 0.012 |
| WEIGHT | 1.1810 | 0.2231 | 5.29 | 0.000 |
| LENGTH 1 | −0.4778 | 0.2345 | −2.04 | 0.050 |
| S = 6.601  R-SQ = 58.7%  R-SQ(ADJ) = 54.8% |||||

| % FAT= 17.5 + 0.0432 BODY RESISTANCE + 1.45 WEIGHT − 0.713 HEIGHT |||||
|---|---|---|---|---|
| PREDICTOR | COEF | SE COEF | T | P |
| CONSTANT | 17.517 | 5.968 | 2.94 | 0.006 |
| BODY RES | 0.04316 | 0.01179 | 3.66 | 0.001 |
| WEIGHT | 1.4510 | 0.1926 | 7.53 | 0.000 |
| HEIGHT | −0.7126 | 0.1728 | −4.13 | 0.000 |
| S = 5.668  R-SQ = 69.5%  R-SQ(ADJ) = 66.7% |||||

| % FAT= 17.2 + 0.0429 BODY RESISTANCE + 1.44 WEIGHT − 0.725 HEIGHT + 0.025 LENGTH 1 |||||
|---|---|---|---|---|
| PREDICTOR | COEF | SE COEF | T | P |
| CONSTANT | 17.204 | 6.855 | 2.51 | 0.018 |
| BODY RES | 0.04291 | 0.01224 | 3.51 | 0.001 |
| WEIGHT | 1.4436 | 0.2100 | 6.88 | 0.000 |
| HEIGHT | −0.7253 | 0.2180 | −3.33 | 0.002 |
| LENGTH 1 | 0.0249 | 0.2543 | 0.10 | 0.923 |
| S = 5.758  R-SQ = 69.6%  R-SQ(ADJ) = 65.6% |||||

FIG. 21

METHOD AND APPARATUS FOR MEASURING BODY FAT IN ANIMALS

FIELD OF THE INVENTION

The present invention relates to methods and apparatus for use in veterinary practice, and more particularly to methods and apparatus utilizing bioelectric impedance analysis (BIA) for measurement of body composition parameters such as body fat, total body water, fat free mass, and/or lean body mass.

BACKGROUND OF THE INVENTION

Many people are concerned about fat levels in their pets. It has been estimated that between 25% and 30% of dogs seen by veterinarians are overweight. Obesity in canines has been linked to many serious health issues including heart disease, diabetes, arthritis, respiratory problems, skeletal stress, gastrointestinal disorders, and skin disorders. These are serious issues, but canine obesity can be difficult to diagnose.

One known method for measuring the body fat of a dog is a "rib check," which entails running one's hand down the ribs and feeling for excess tissue. Most pet owners do not perform this simple test. Moreover, rib checks are subjective in nature and the accuracy of the test (i.e., the determination of the presence and amount of excess fat) depends largely upon the expertise of the handler. Thus, many pet owners distrust the results of this method, even if performed by an experienced and qualified veterinarian.

Many veterinarians and other pet health professionals, in addition to a rib check, may score a dog's obesity utilizing a body condition chart. This chart provides some uniformity, but the results are essentially the same as those of the rib check.

Another method to measure body fat in dogs is DEXA (dual energy X-ray absorptiometry) analysis. This method entails anesthetizing the dog and performing a 15-minute full body X-ray to determine bone/body density. This method is invasive, time consuming, and expensive. Although the results are very accurate, it is not practical to use such a method in ordinary veterinary check-ups or grooming visits.

In recent years, bioelectric impedance analysis (BIA) has gained acceptance as a method for measuring body fat percentage in humans. Scales have been developed utilizing this technology and are available for consumer purchase. Referring to prior art FIG. 9, BIA utilizes two sets of electrodes 142, 144 and 146, 148 connected to the tissue 150 of a subject 166, one set at each of two separate locations 152, 154. A very small, high frequency electrical current 174 is sent from a sinusoidal constant current source 172 between two outermost electrodes 142, 148, which are current source electrodes. This current is small enough to be harmless and undetectable to the subject. Two inner electrodes 144 and 146 act as detecting electrodes and a high input impedance, phase sensitive voltmeter 178 measures a voltage drop and phase lag due to tissue 150 between the two sets of electrodes 142, 144 and 146, 148. The voltage drop is due to the resistance R of tissue 150 and the phase difference is due to the capacitance C of tissue 150. The combination of these two values yields the total impedance of tissue 150. Fatty tissue will have a higher impedance than lean tissue.

Studies have indicated that BIA theory might also be applied to dogs. However, known studies utilized subcutaneous needles to attach electrodes to dogs in conjunction with general anesthesia. These techniques are highly invasive and quite expensive to perform. Moreover, previous studies have lead at least one researcher to conclude that "[n]o useful correlation between impedance measurements involving one or two limbs and major body components has been demonstrated either in the present study . . . or other studies." (Burkholder, pp. 202). Burkholder found that legs of dogs (which are not generally areas of fat deposits for canines) typically have ten times more resistance than the torso, making it difficult for BIA devices to distinguish between the desired torso impedance measurement (approximately 100 ohms) and the leg impedance (approximately 1,000 ohms.) Therefore, measurements through the legs were not found to correlate well with body fat.

SUMMARY OF THE INVENTION

One configuration of the present invention therefore provides an apparatus for measuring at least one body composition measure of an animal. The apparatus includes a mat having four pairs of electrodes on its surface, wherein each electrode pair is configured to contact a different paw of an animal standing on the mat. The apparatus also includes electronic circuitry electrically coupled to the four pairs of electrodes and configured to utilize the four pairs of electrodes to measure a first impedance of the animal standing on the mat through one front paw of the animal and one rear paw of the animal and a second impedance of the animal standing on the mat though both front paws of the animal in parallel and both rear paws of the animal in parallel. The electronic circuitry includes a processor configured to determine the body composition measure of the animal utilizing the first measured impedance and the second measured impedance.

In another configuration, the present invention provides a method for determining a relationship between body impedance of an animal and a body composition measure of an animal. The method includes steps of measuring a first electrical impedance between a front foot pad of the animal and a rear foot pad of the animal; measuring a second electrical impedance between two front foot pads of the animal in parallel with one another and two rear foot pads of the animal in parallel with one another; determining a torso impedance of the animal using the first measured impedance and the second measured impedance; repeating the measuring of the first impedance, the measuring of the second impedance, and then determining the torso impedance for a plurality of animals of the same species; obtaining a second, independent determination of the body composition measure of the plurality of animals; performing a regression analysis using the second, independent determination of the body composition measure to determine a relationship between the body composition measure and variables including torso impedance; and programming a processor to determine the body composition measure of an animal utilizing impedance measurements of an animal and the determined relationship.

In yet another configuration, the present invention provides a method for measuring a body composition measure of an animal. The method includes steps of measuring a first electrical impedance between a front foot pad of the animal and a rear foot pad of the animal; measuring a second electrical impedance between two front foot pads of the animal in parallel with one another and two rear foot pads of the animal in parallel with one another; and utilizing the first electrical impedance, the second electrical impedance, and a regression relationship to determine the body composition measure of the animal.

Configurations of the present invention thus provide non-invasive diagnostic testing of animals for body composition measures such as body fat, and are of particular use in estimating body fat in dogs. Configurations of the present invention described herein are practical for use in a veterinary office, and can be used by veterinarians for diagnosing obesity in pet animals, including dogs. Many configurations of the present invention provide results that are more accurate, objective, and uniform than other methods commonly used by pet health professionals without requiring anesthetizing the animal or the use of X-rays. Measurements can be taken without producing discomfort for the animal being measured. Even if the animal experiences general anxiety from being brought to a veterinary office for examination, that general anxiety can be relieved by the animal's owner in configurations of the present invention that allow the owner to comfort the animal by his or her touch even as measurements are being taken.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3 is a top plan view of a mat incorporating an electrode array.

FIG. 7 is a schematic representation of an electrical circuit equivalent to that through a dog from one of its front paws to one of its rear paws.

FIG. 8 is a schematic representation of an electrical circuit equivalent to that through a dog from both of its front paws in parallel to both of its rear paws in parallel.

FIG. 9 is a simplified electrical block diagram of a body impedance analysis (BIA) of an animal, as is known in the prior art.

FIG. 11 is a table of raw zoometric data for the dogs used in-determining the empirical relationship shown in FIG. 10.

FIG. 12 is a table of BCS scores and additional raw zoometric data for the dogs used in determining the empirical relationship shown in FIG. 10.

FIG. 13 is a table of measured four paw impedances for the dogs listed in FIGS. 11 and 12.

FIG. 14 is a table of measured two paw impedances for the dogs listed in FIGS. 11 and 12.

FIG. 15 is a table of resistances and capacitances, including torso resistances and torso capacitances, derived from the measurements listed in FIGS. 13 and 14.

FIG. 16 is a table comparing the percentage body fat for each dog obtained utilizing the dual energy X-ray absorptiometry (DEXA) method and those utilizing the body impedance analysis (BIA) regression equation obtained from the dogs listed in FIGS. 11 and 12 from the regression results of FIG. 10 obtained utilizing the torso impedance obtained in FIG. 15.

FIG. 20 is a table showing additional regression equations, variables, and measures showing how well the equations fit the observations.

FIG. 21 is a table showing still more regression equations, variables, and measures showing how well the equations fit the observations.

DETAILED DESCRIPTION OF THE PREFERRED EMBODIMENTS

The following description of the preferred embodiment(s) is merely exemplary in nature and is in no way intended to limit the invention, its application, or uses.

Figure 1:
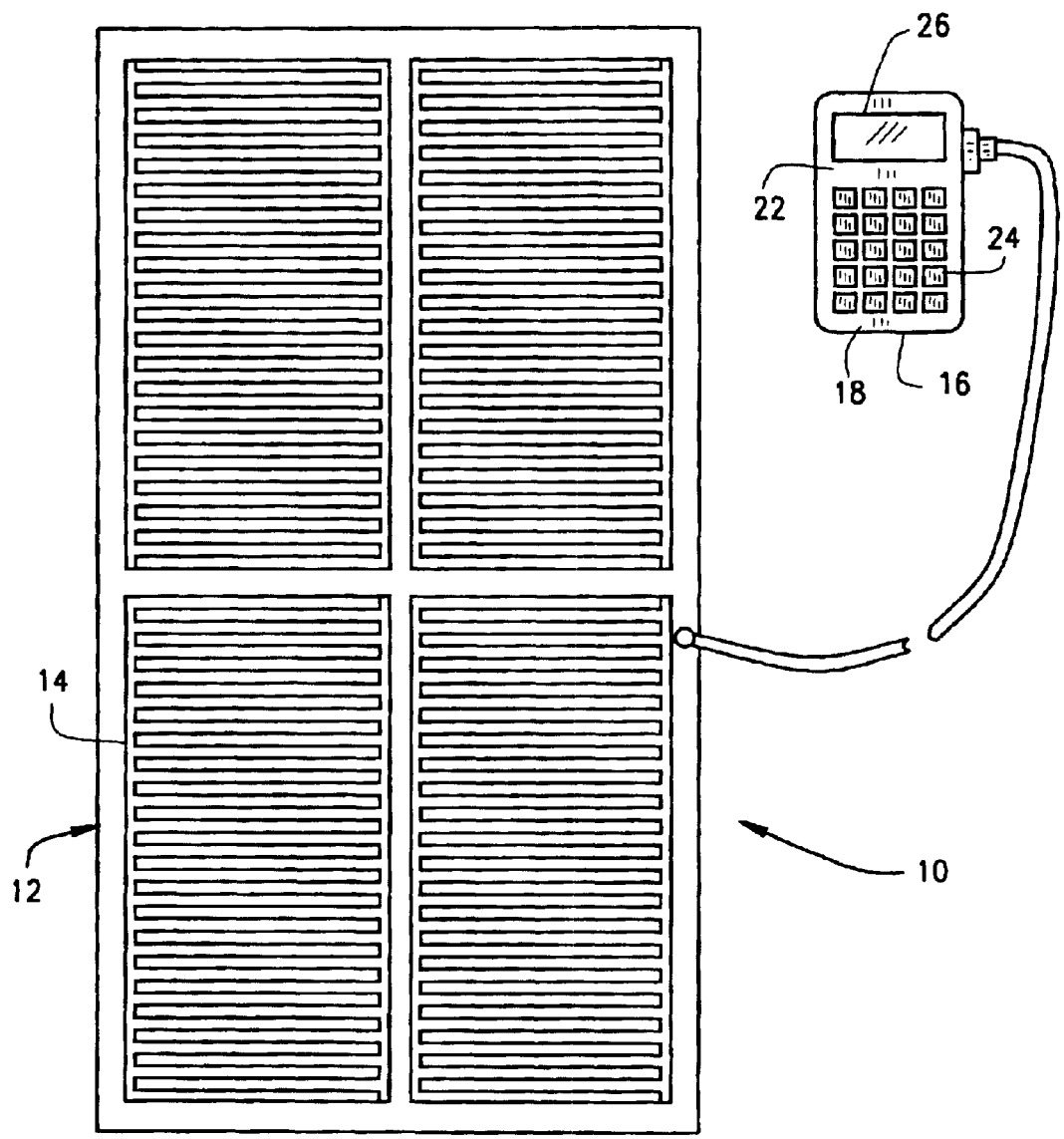
FIG. 1 is a pictorial drawing of one configuration of the present invention.
Figure 2:
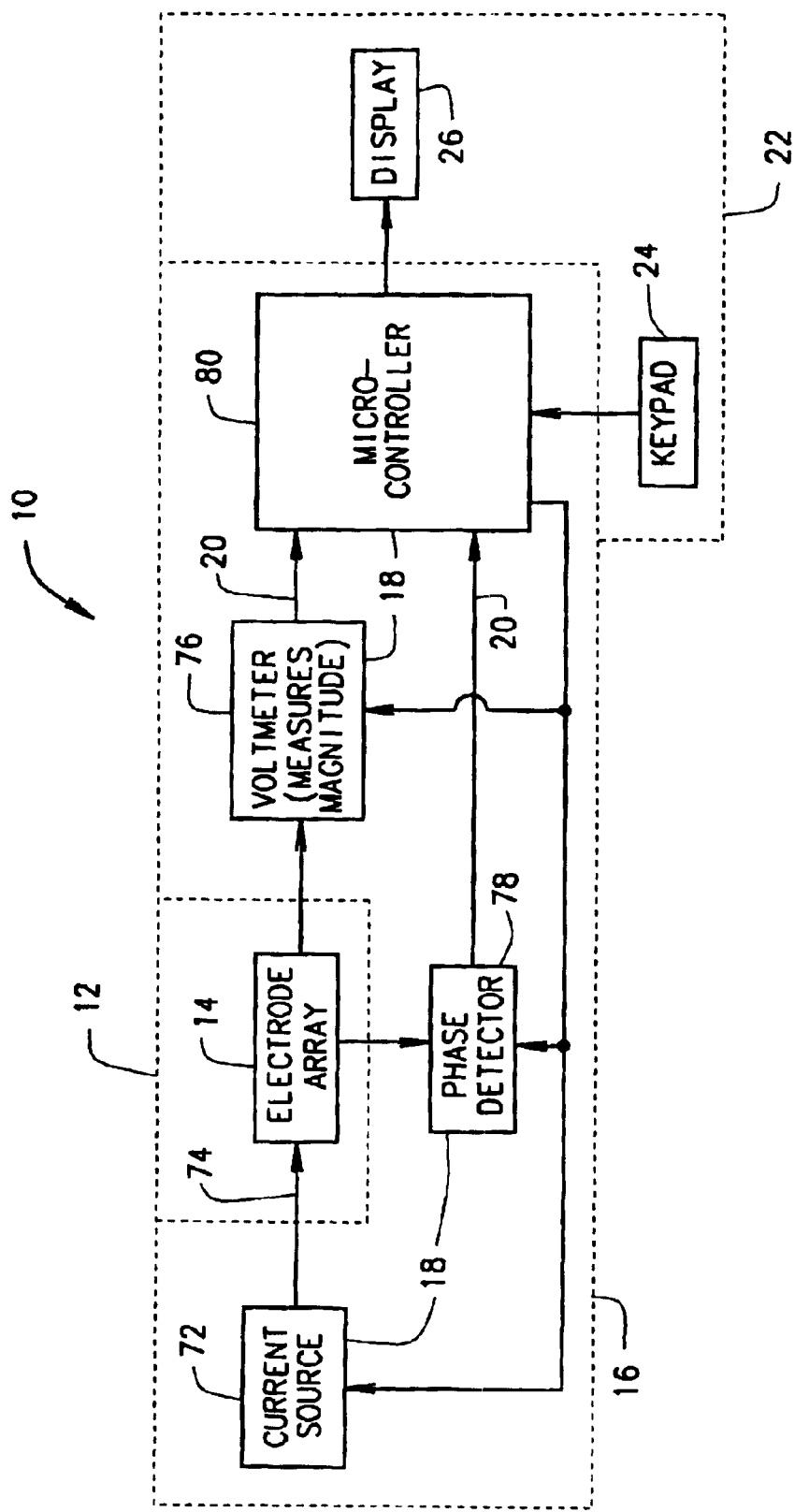
FIG. 2 is a schematic block diagram of the configuration of the present invention represented in FIG. 1.

In one configuration of the present invention and referring to FIGS. 1 and 2, an apparatus 10 to measure body fat utilizing BIA technology is provided. Apparatus 10 comprises three subsystems. A first subsystem 12 comprises an electrode array 14 that electrically connects body fat measuring apparatus 10 to an animal being measured (not shown in FIGS. 1 and 2). A second subsystem 16 comprises electronic circuitry 18 that creates one or more electrical signals 20 indicative of a ratio of body fat to body weight of the animal being measured and that determines an amount or percentage of body fat utilizing a predetermined relationship. A third subsystem 22 comprises a user interface 24 that enables a user to enter information used in the body fat determination and that provides a human-readable display 26 of body fat percentage.

Figure 3:
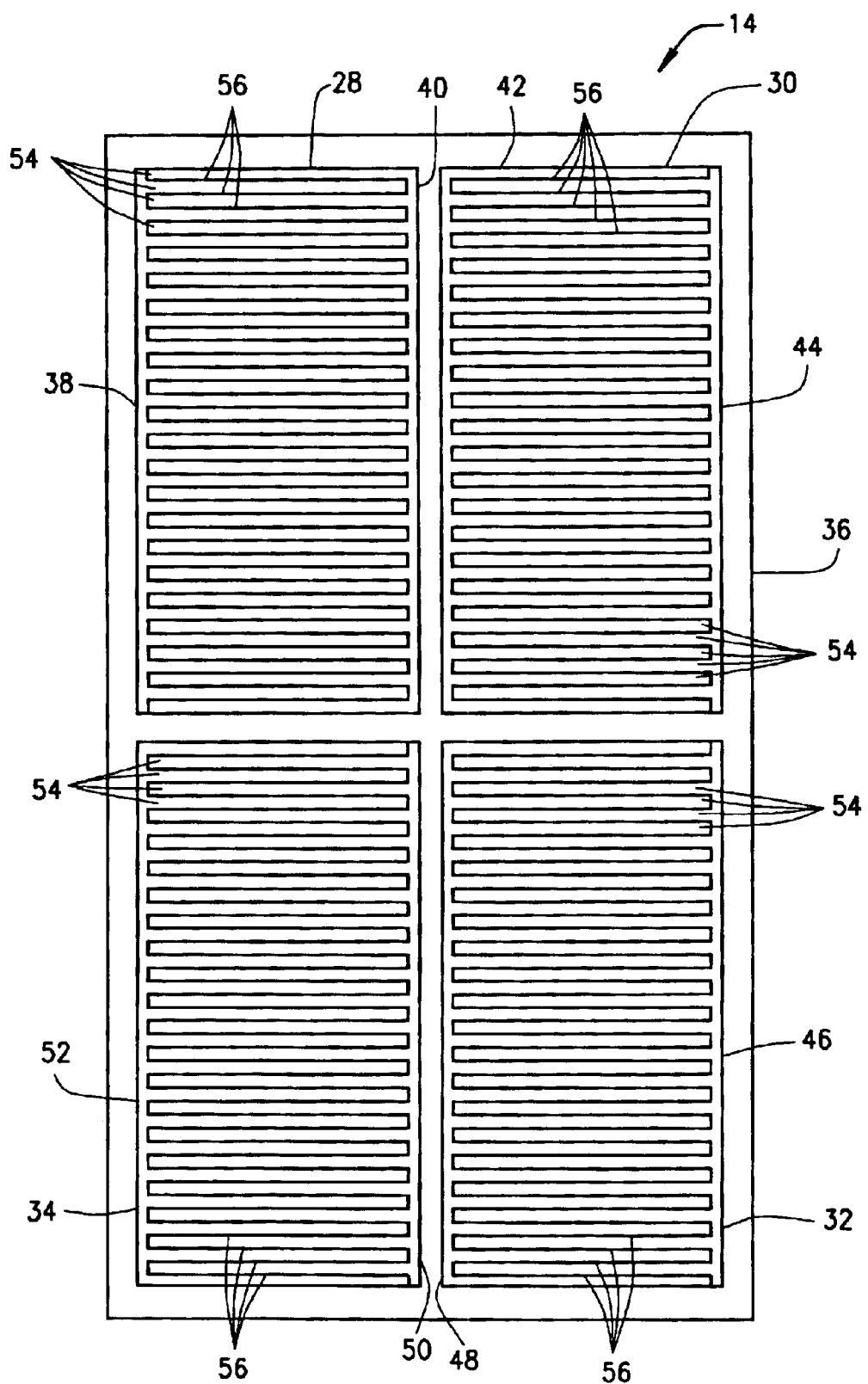
FIG. 3 is a top plan view of a portion of the configuration represented in FIG. 1; more specifically.

Electrode array 14 comprises a plurality of electrodes 38, 40, 42, 44, 46, 48, 50, 52 configured to provide skin contact to the bottom of an animal's paw or foot. In one configuration and referring to FIG. 3, electrode array 14 comprises four pairs 28, 30, 32, 34 of electrodes, each pair affixed to a different portion (e.g., a different quadrant) of a rectangular non-conducting sheet or mat 36. Each pair 28, 30, 32, 34 of electrodes is interdigitated. Pairs 28, 30, 32, and 34 cover separate areas or quadrants of mat 36 so that a dog placed on mat 36 can comfortably stand with each paw on a different electrode pair 28, 30, 32, and 34. (In one configuration, other mat and electrode pair sizes are supplied for other types of animals.) In one configuration, each pair 28, 30, 32, 34 of interdigitated electrodes comprise metallic conductors cut or otherwise formed from a single sheet of material, such as aluminum. Interdigitated electrodes 38, 40, 42, 44, 46, 48, 50, and 52 are configured to provide contact to both electrodes in each pair on each paw of an animal placed on sheet or mat 36 (e.g., both electrodes 38 and 40 in electrode pair 28), and sheet or mat 36 is configured so that an animal placed on it will have one paw on each quadrant, and thus one paw on each pair 28, 30, 32, 34 of interdigitated electrodes. The paws of a dog placed on mat 36 in this manner have been found by the inventors to provide sufficient skin contact to the electrode surfaces to obtain reliable impedance measurements because of the relative absence of fur or hair on the dog's paws. Moreover, by providing two electrodes that contact the animal at each paw, BIA requirements are met for having one electrode to supply a signal and another to measure the impedance of the animal at a contact point. Because the electrodes of each interdigitated pair of electrodes are closely spaced (e.g., electrodes 38 and 40 of pair 28), contact with a paw is maintained regardless of where the dog may place its paw on the electrode pair. However, one paw of the dog must be placed on each pair 28, 30, 32, 34 of electrodes. When the dog (or other animal) has paws positioned in this manner, one paw would contact both electrodes 38 and 40, a second paw would contact electrodes 42 and 44, a third paw would contact electrodes 46 and 48, and a fourth paw would contact electrodes 50 and 52.

In one configuration, each of the interdigitated pairs of electrodes comprises a 9 in by 18 in (22.86 cm by 45.72 cm) area, and electrodes 38, 40, 42, 44, 46, 48, 50, and 52 are 1/32 in (0.079375 cm) thick aluminum sheet metal attached to a single 1/4 in (0.635 cm) thick piece of ABS plastic 36. The overall dimensions of plastic mat 36 are 21 in by 39 in (53.34 cm by 99.06 cm). These dimensions are consistent with standard veterinarian scales and are large enough to fit essentially any dog. Electrodes 38, 40, 42, 44, 46, 48, 50, and 52 are each configured to have a large surface area. Electrodes with small gaps between relatively wide fingers provide a suitably large electrode surface area while still allowing each paw to contact each electrode of a pair of electrodes. Thus, in one configuration, fingers 54 of the interdigitated electrodes are 0.4375 in (1.11125 cm) wide and gaps 56 between fingers 54 are only 0.050 in (0.127 cm).

In another configuration, a thinner plastic mat 36 is utilized along with thinner electrodes 38, 40, 42, 44, 46, 48, 50, and 52. To practice the present invention, it is not required that mat 36 be made of ABS plastic or that electrodes 38, 40, 42, 44, 46, 48, 50, and 52 be made of aluminum. Other insulating materials may be used instead of, or in combination with, ABS plastic, and other conductors may be used instead of, or in combination with, aluminum. For example, in yet another configuration, mat 36 is a flexible, non-conductive plastic or rubber membrane, and electrodes 38, 40, 42, 44, 46, 48, 50 and 52 are silk-screen printed conductive paint. This latter configuration provides convenient handling and storage, and may even be rolled up when not in use.

Figure 4:
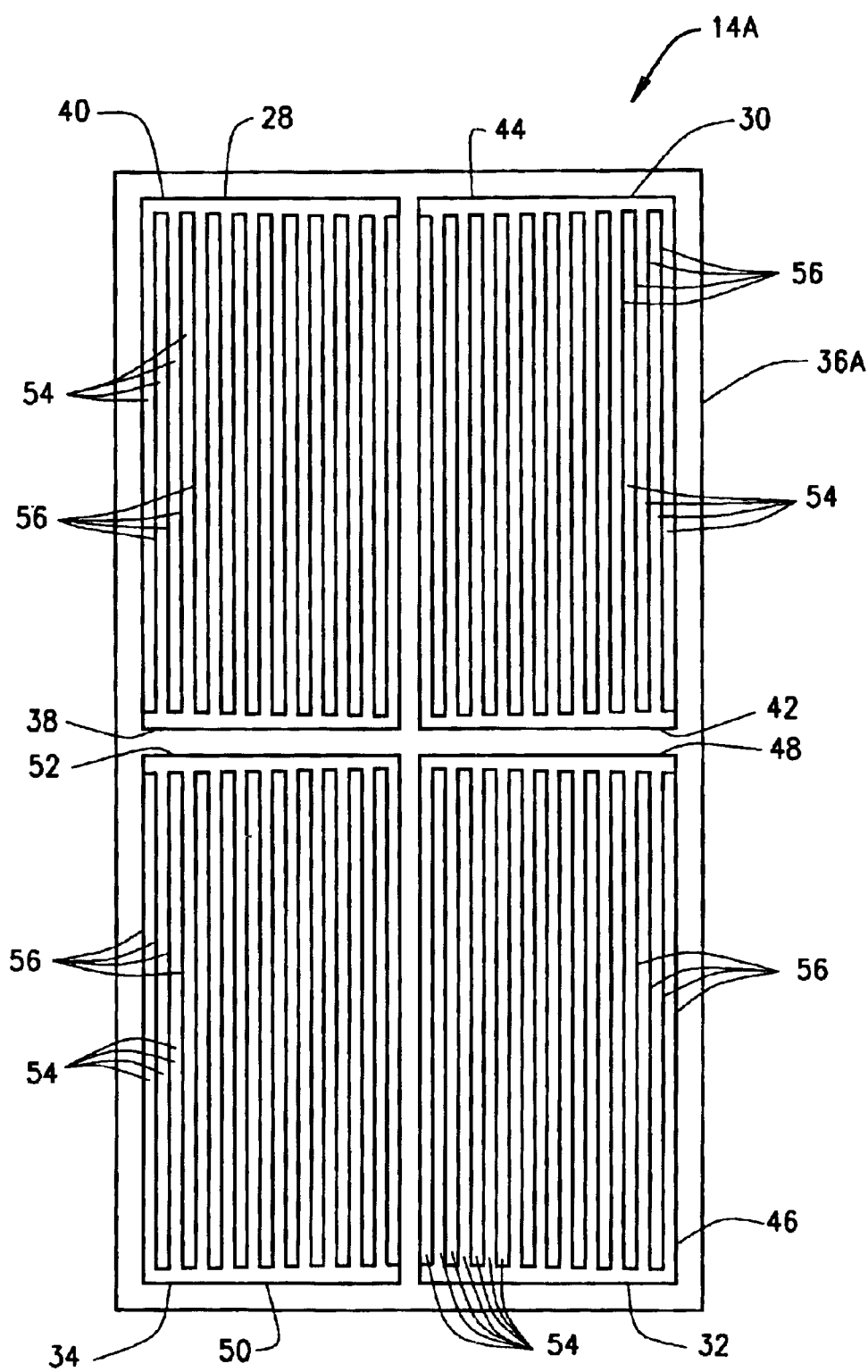
FIG. 4 is a top plan view of an alternative configuration of a mat incorporating an electrode array.

The orientation of interdigitated electrode fingers 54 is not critical for practicing the present invention. For example, in one configuration and referring to FIG. 4, fingers 54 of mat 36A are oriented perpendicularly to fingers 54 of mat 36 in FIG. 3. However, electrode array 14A and mat 36A can be substituted for electrode array 14 and mat 36 for practicing the present invention. Other configurations of electrode pairs are also useful for the present invention. Not all of these configurations comprise interdigitated electrode pairs, but many are configured to provide electrical contacts for both electrodes to a paw of an animal under test, wherein the electrical contacts are of sufficiently low impedance to allow the BIA test described below to be performed. In addition, many of the configurations of electrodes provide a large surface area over which such contacts can be made, so that critical positioning of the paws of the animal is not required. For example, and referring to FIGS. 5 and 6, each pair 28, 30, 32, 34 of electrodes covers a different surface area of mat 36. Each paw 58, 60, 62, 64 of a dog 66 to be tested is placed on a different area of mat 36, and thus each paw 58, 60, 62, and 64 contacts a different pair of electrodes, in this case, respectively 28, 30, 32, and 34. Each electrode on mat 36 is separately electrically connected to a connecting unit housing 68 on mat 36 via any suitable means (for example, connecting wires or traces embedded in or on the surface of mat 36, between connecting unit housing 68 and each electrode). Cables, such as multiconductor cable or cables 70 conduct electrical signals between electrodes on mat 36 and second subsystem 16, which comprises a hand-held unit 82 in the illustrated configuration. In another configuration, electronics and/or interface elements of second subsystem 16, are incorporated into connecting unit housing 68, so that no cabling or hand-held unit is required. In yet another configuration, a portion of the electronic circuitry of FIG. 2 (e.g., voltmeter 76, phase detector 78, and current source 72) are incorporated into housing 68 along with a wireless remote control receiver and transmitter (not shown), so that cables 70 are not required. The portion of electronic circuitry in housing 68 is wired to the electrodes of electrode array 14 on mat 12. In this configuration, hand-held unit 82 contains another portion of the electronic circuitry of FIG. 2 (e.g., microcontroller 80, keypad 24 and display 26) and also comprises a wireless remote control transmitter and receiver, thereby permitting a user to enter and view data and control the apparatus without the movement restrictions and inconvenience of cables 70. The wireless remote control receivers and transmitters may, for example, be radio or infrared receivers and transmitters.

Electrode array 14 is electronically configured in two different ways to take two different impedance measurements of the dog. In one measurement and referring to FIGS. 2, 6 and 7, one of electrode pairs 28 and 30 and one of electrode pairs 32 and 34 are turned off (i.e., not excited by current source 72 and not measured by voltmeter 76 and phase detector 78) and the body impedance is measured through one front leg 84 or 86 and one rear leg 88 or 90. For example, electrode pairs 28 and 34 are selectively turned off (i.e., not energized by current source 72, under control of processor 80), and one electrode of each of electrode pairs 30 and 32 is turned on (i.e., selectively energized by current source 72, under control of processor 80) so that the body impedance of animal 66 through legs 86 and 90 is measured between paw 60 and paw 62, which are on electrode pair 30 and 32, respectively. In the other measurement, and referring to FIGS. 2, 6, and 8, one electrode of each of the four electrode pairs 28, 30, 32, and 34 is turned on (i.e., energized by current source 72, under control of processor 80) and the body impedance of animal 66 is measured through legs 84 and 86 together and legs 88 and 90 together using both front legs 58 and 60 in parallel and rear legs 62 and 64 in parallel. Phase detector 78 and voltmeter 76 are each coupled to an electrode of electrode pairs 28, 30, 32, and 34 different from the one coupled to current source 72, so that the impedance of the animal can be measured. In this manner, two different impedance measurements are obtained, one of which is represented by $Z_{front\_leg}+Z_{torso}+Z_{rear\_leg}$, as illustrated in FIG. 7, and the other of which is $Z_{front\_legs\_parallel}+Z_{torso}+Z_{rear\_legs\_parallel}$, as illustrated in FIG. 8. In one configuration of the present invention, two equations with these two impedance measurements are utilized to solve for the torso impedance of the animal. A predetermined relationship between the torso impedance obtained in this manner and body fat percentage is then used to determine a percentage of body fat for the subject animal. More particularly, if $Z_2=Z_{front\_leg}+Z_{torso}+Z_{rear\_leg}$, $Z_4=Z_{front\_legs\_parallel}+Z_{torso}+Z_{rear\_legs\_parallel}$, and it is assumed that both front legs have the same impedance and both rear legs have the same impedance, then $Z_4=Z_{front\_leg}/2+Z_{torso}+Z_{rear\_leg}/2$. Combining the latter equation with the equation for $Z_2$, an expression for $Z_{torso}$ is obtained: $Z_{torso}=2(Z_4)-Z_2$. Using this last equation, it is possible to arrive at impedance values for the torso alone by measuring two impedances, one measured from one front leg to one rear leg ($Z_2$) and the other measured from both front legs in parallel to both rear legs in parallel ($Z_4$), In one configuration and referring to FIGS. 2 and 9, electronic circuitry 16 comprises an analog current source 72 that is configured to generate a high-frequency, low current signal 74 that is sent through an animal via electrodes on electrode array 14, including, for example, electrodes 42 and 48. Electronic circuitry 16 also comprises a voltmeter 76 and phase detector 78 that measure voltage and phase differences, respectively, resulting from the impedance of an animal standing on electrode array 14, using electrodes such as electrodes 44 and 46. A digital processor, for example, an eight-bit microcontroller 80 is configured to control current source 72, voltmeter 76, and phase detector 78 to generate a current through an animal and measure the resulting voltage and phase differences. Outputs of voltmeter 76 and phase detector 78 are coupled to processor 80, which is configured, utilizing software or firmware (not shown in FIG. 2 or 9) to determine the body fat percentage from the measured voltage and phase differences utilizing a predetermined relationship, and to control display screen 26 (for example, an LCD display screen) that provides a portion of user interface 22. In one configuration, processor 80 contains read only memory (ROM, also not shown in FIG. 2 or 9) in which firmware instructions containing the relationship are contained. Electronic circuitry 16 and LCD display 26 are powered by a suitable power supply (not shown in FIG. 2), such as one using a standard wall outlet as a power source or a replaceable or rechargeable battery as a power source.

In one configuration, circuitry 16 comprises a 60 kHz, 500 µA AC current source 72, a phase sensitive voltmeter (76 and 78), and a power supply (not shown) that is powered from a standard 110 volt wall outlet. AC current source 72 comprises an oscillator configured to produce a 60 kHz sine wave. This sine wave is input to a voltage-to-current amplifier (i.e., a transconductance amplifier, not shown separately from current source 72 in FIG. 2) to ensure that the same current signal is produced regardless of the impedance of the animal being measured.

Phase sensitive voltmeter 76, 78 includes a phase detector 78 and a measuring circuit 76 configured to measure the amplitude of an oscillating signal. Phase detector 78 measures the difference between the sine wave input into the transconductance amplifier and the sine wave that is measured from a second set of electrodes. The sine wave from the second set of electrodes is also input to amplitude measuring circuit 76. The amplitude and phase measurements are then utilized to produce a complex impedance measurement.

In one configuration, circuitry 16 further comprises an 8-bit microprocessor 80 with associated memory such as RAM and/or ROM (not shown), and a keypad or keyboard 24 operatively coupled to microprocessor 80 to receive operator input of zoometric data for the animal being measured. Keypad 24 is of a convenient size for manipulation by an operator. Circuitry 16 also comprises a display, such as LCD 26 operatively coupled to microprocessor 80 to display human-readable output from microprocessor 80. Microprocessor 80 is configured to switch current source 72 on and off to control the application of a signal to, and the measurement from, either two or four of the electrode pairs in electrode array 14. Microprocessor 80 is also configured to control LCD 26 and to accept input from keypad 24.

In one configuration and referring again to FIGS. 1 and 6, circuitry 16 is housed inside a hand-held unit or box 82 about the size of a graphing calculator. To facilitate high volume production and miniaturization, circuitry 16 in one configuration is implemented utilizing surface-mount components mounted on a printed circuit board. Keypad 24 is mounted on hand-held box 82, and LCD 26 is mounted in or on hand-held box 82 in such a manner as to be visible to the operator while the operator is entering data via keypad 24. In one configuration, insulated multiconductor flexible cable or cables 70 are about 6 ft (182.88 cm) long and connect circuitry 16 to electrodes 38, 40, 42, 44, 46, 48, 50, and 52 on mat 36. In another configuration, circuitry 16 is integrated onto mat 36 and protected by a suitable housing such as housing 68. To use the apparatus, the user uses keypad 24 to enter the weight, thorax girth, and abdomen girth of an animal being measured. The animal is placed on mat 36 to perform the impedance measurements. These impedance measurements are then used by microprocessor 80, along with the information entered by the user, to determine a body fat percentage for the animal utilizing the predetermined relationships. Microprocessor 80 displays the determined body fat percentage on LCD display 26.

To measure body fat accurately utilizing impedance measurements, a relationship between measured body impedance and body fat has been determined. In one configuration of the present invention, this relationship is used as the predetermined relationship referred to above for converting measurements made on an animal under test into a body fat percentage relating to that animal.

Figures 10, 17:
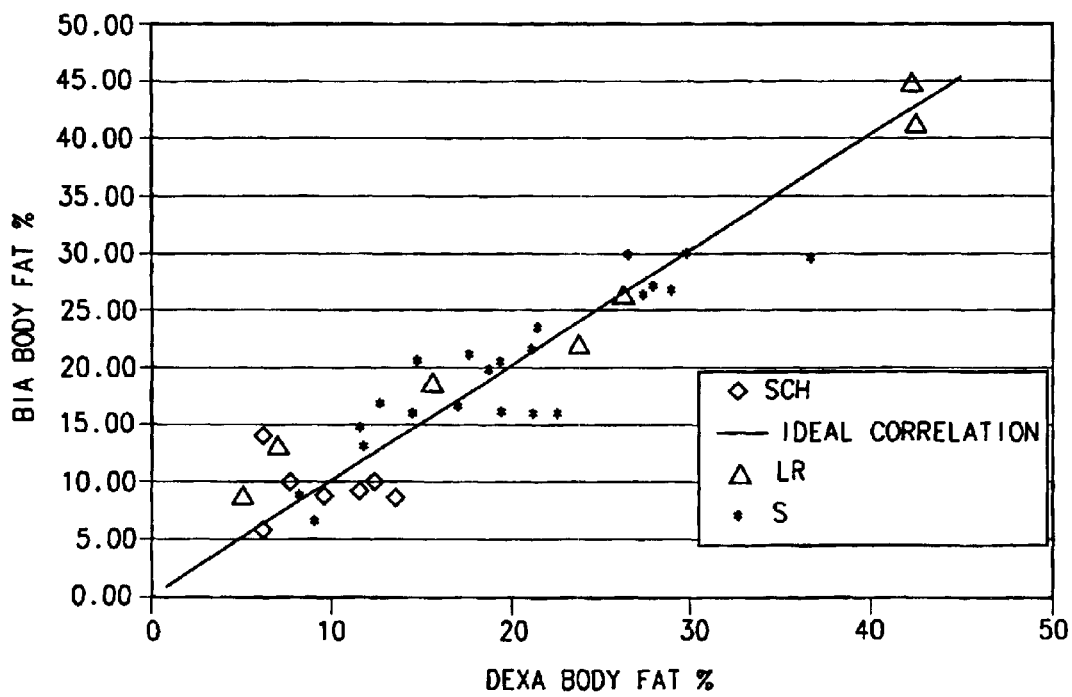
FIG. 10 is a table showing an empirical regression relationship obtained from experimental measurements of torso impedance (and thus, body resistance) from a selected group of dogs utilizing a configuration of an apparatus of the present invention.
FIG. 17 is a graph fitting the BIA regression equation to the DEXA values.

Thirty-five dogs were tested using a medical grade impedance measuring device from RJL systems. The same dogs were tested utilizing a configuration of an electrode map of the present invention. The same dogs were also measured using DEXA (dual energy X-ray absorptiometry). Utilizing the DEXA total body fat percentage measurements as a standard, an empirically determined regression relationship equation relating impedance to body fat was derived utilizing a step-wise regression. This relationship was found to be:

$$\% \text{ BodyFat} = -27.2 - (2.16 \times \text{Weight}) + (2.85 \times \text{AbdomenGirth}) + (0.0326 \times \text{BodyResistance}) - (67.7 \times \text{AbdomenGirth}/\text{ThoraxGirth}),$$

wherein Weight is the weight of the dog in kilograms, AbdomenGirth is the abdomen girth in centimeters, BodyResistance is the real part of the determined torso impedance in ohms, and ThoraxGirth is the thorax girth in centimeters. Referring to FIG. 10, the $R^2$ value obtained from this regression was 0.874, which represents a substantial improvement over predictions using zoometric data alone. The P-values of the predictors in this are shown in FIG. 10. In each case, the value is less than 0.1%, meaning that there is nearly 100% confidence that these values are significant predictors of body fat.

Negative coefficients in the relationship may arise because some variables may overestimate the body fat, so that other variables may have to be subtracted to obtain the most accurate prediction. Another possible explanation for negative coefficients is that for a given volume, lean tissue weighs more than fatty tissue. Thus, on a volume basis, a greater weight indicates a smaller percentage of body fat. Either or both of these explanations may explain the presence of negative coefficients in the relationship, or some completely different explanation may apply. However, an explanation is not required to practice the invention, as the predictive power of the relationship is statistically evident.

FIGS. 11 and 12 are tables of raw zoometric data and body condition scores (BCS) for the dogs used in determining the empirical relationship shown in FIG. 10. (In FIG. 11, "Breed" is either SCH, LR, or S, referring to miniature schnauzer, Labrador retriever, and English setter, respectively. Body condition scores were obtained in accordance with Laflemme, DP, "Body Condition Scoring and Weight Maintenance," Proc. N. Am. Vet. Conf., January 16–21, 1993, Orlando, Fla., pp. 290–291, which is hereby incorporated by reference in its entirety.) FIG. 13 is a table of measured four-paw impedances for the same dogs measured utilizing one configuration of the present invention, with the dog placed on an electrode array mat. Three measurements were made for each dog. FIG. 14 is a table of measured two-paw impedances for the same dogs measured utilizing the same configuration of the present invention. Again, three measurements were made for each dog. FIG. 15 is a table of measured resistance and capacitance for these dogs, as determined from the measurements shown in FIGS. 13 and 14. An average value was determined from the repeated measurements. (Single measurements could be used without averaging, although with some risk of less accurate results.)

More generally, to determine a relationship between body impedance of an animal and body fat of an animal, a first electrical impedance is measured between a front foot pad of the animal and a rear foot pad of the animal, for example, by standing the animal on the apparatus of FIGS. 1 and 2. A second electrical impedance is measured between two front foot pads of the animal in parallel with one another and two rear foot pads of the animal in parallel with one another. In one configuration, both the first measured impedance and the second measured impedance are measured as complex impedances. A torso impedance of the animal is determined using the first measured impedance and the second measured impedance, for example, using the relationship $Z_{torso}=2(Z_4)-Z_2$ as discussed above. These steps are repeated for a plurality of animals of the same species (e.g., dogs). An independent determination of the body fat of the plurality of animals is also obtained, such as by using the DEXA technique. (By "independent," it is meant that this determination is obtained other than by using the first impedance measurement and the second impedance measurement.) A regression analysis is performed using the independent determination of the body fat to determine a relationship between body fat and variables including torso impedance. The regression analysis may include raw zoometric data for the animals as well as measured impedances. This regression relationship can then be programmed into a processor, such as processor 80, with other instructions to instruct the processor to determine body fat of an animal utilizing impedance measurements of the animal and the determined relationship.

Microprocessor 80 is not limited to utilizing a regression equation solely to determine percentage body fat. Microprocessor 80 may utilize one or more other regression equations in addition to, or in place of the body fat percentage regression equation. Thus, some configurations of the present invention are more generally useful for determining body composition measures. These body composition measures may include one or more body composition measures in addition to, or in place of body fat percentage. Note that the regression analysis techniques described above can be used to determine regression equations for these other body composition measures, for example, total body water, fat free mass, lean body mass, and body fat, either as an absolute amount or as a percentage of total body weight.

FIG. 16 is a table comparing the percentage body fat for each dog obtained by the DEXA method and by the BIA equation utilizing the regression results that were presented in FIG. 10. FIG. 10 includes coefficients of the predictors, standard errors of the coefficients, T- and P-values, and $R^2$ values.

Figure 18:
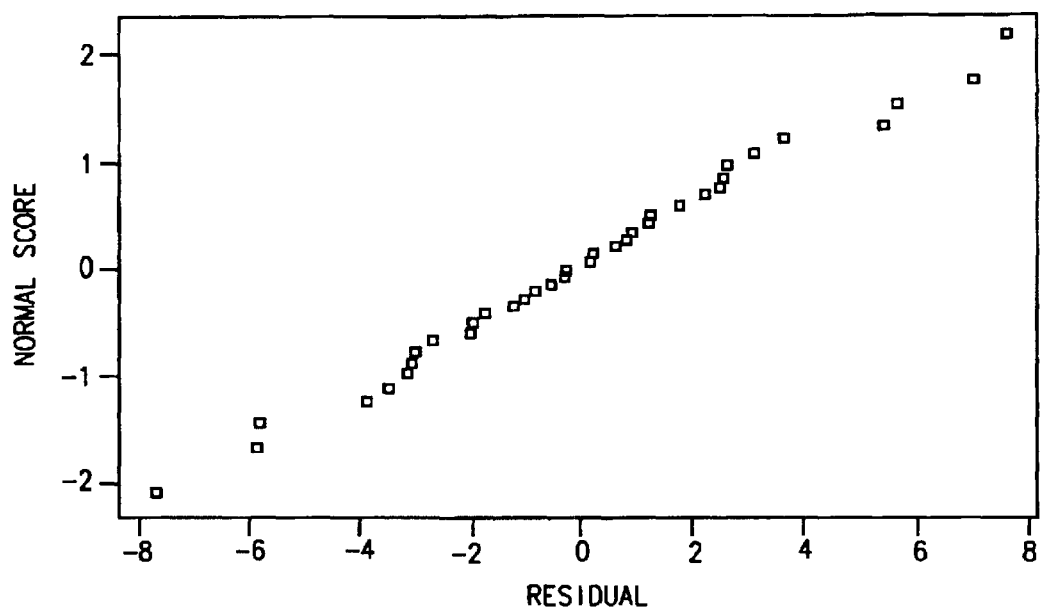
FIG. 18 is a normal probability plot of residuals for the regression equation shown in FIG. 10.
Figure 19:
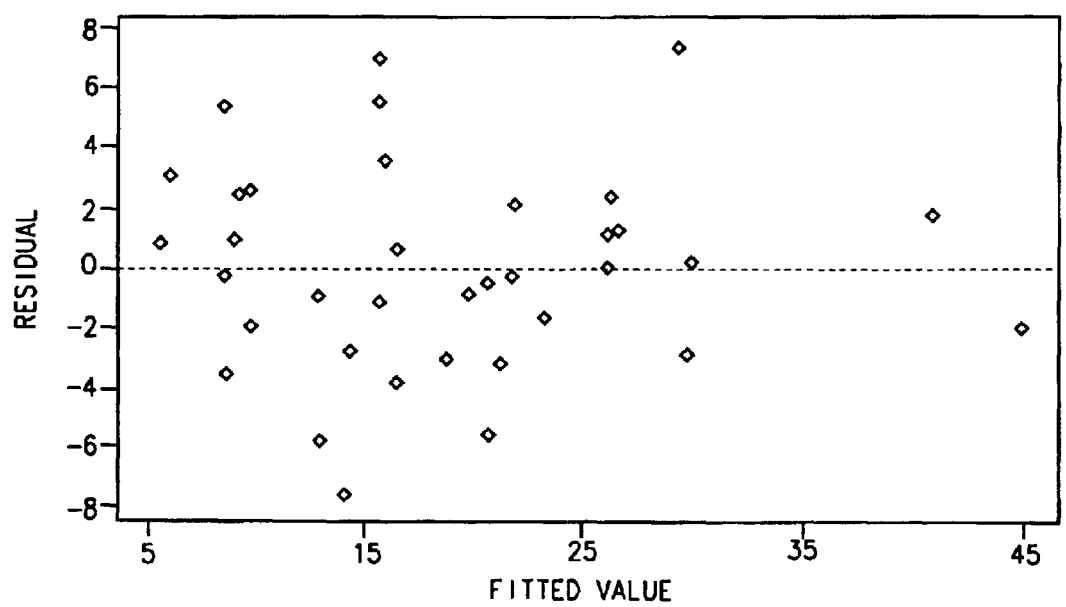
FIG. 19 is a plot of residuals vs. fitted values.

FIG. 17 is a graph fitting the BIA regression equation to the DEXA values, wherein the diagonal line represents perfect or 100% correlation, and SCH, LR, and S refer to data point for miniature schnauzers, Labrador retrievers, and English setters, respectively. Most of the data fits very close to the diagonal line and follows the correct trend. FIG. 18 is a normal probability plot of residuals for the regression equation. The nearly linear distribution of residuals indicates that a linear regression fits the data very well. FIG. 19 is a graph of residuals vs. fitted values. The random scattering of points indicates that there is no significant trend in the data that has not been predicted by the regression equation.

Although the regression fitting for this example utilized a limited number of dogs and a limited number of breeds, other configurations of the present invention may utilize additional dogs, additional breeds, and more dogs with a higher percentage of body fat than used in this example to provide an improved and/or more complete empirical correlation. The practice of the present invention is also not limited to regression equations using only the variables in FIG. 10. Other combinations of regression variables may be used, such as the examples provided in FIGS. 20 and 21. Some of these regressions provide $R^2$ values nearly as good as those of the regression of FIG. 10 using the same data. Because the regression is statistical rather than deterministic, it is possible that one or more of these regressions may provide improved results relative to the regression of FIG. 10 for a larger and/or more complete sample of dogs selected for testing. Note that in one of the regressions shown in FIG. 20, a variable ρ(rho, i.e., resistivity) is used. This variable is defined by:

$$\rho=(Z_{torso} \times \text{AbdominalGirth}^2)/(4 \times \pi \times \text{Length})$$

However, the results in the corresponding regression in FIG. 20 show that ρ is not significant in the regression equation.

Figure 6:
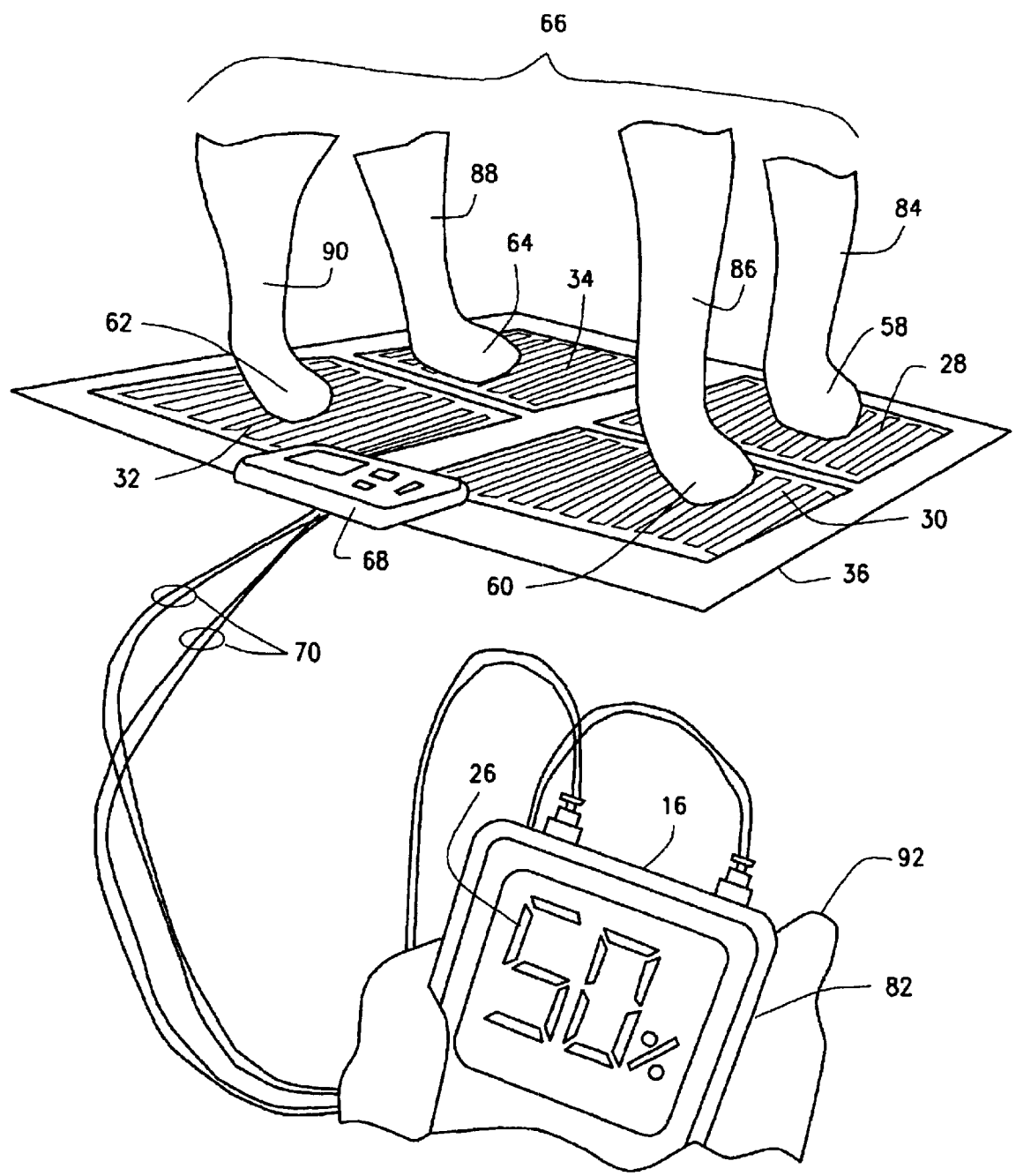
FIG. 6 is a pictorial view representing the measurement of body fat of a dog positioned as represented in FIG. 5.

To use one configuration of the present invention to measure a percentage of body fat in a dog's body, mat 36 is connected to the controller using appropriate wires such as flexible multiconductor cable or cables 70 shown in FIG. 6. An AC adapter (not shown) is plugged into hand-held controller 82 and into a standard wall outlet. An operator 92 of controller 82 enters values required by the predetermined regression equation into controller 82 via keypad 24, shown in schematic block diagram form in FIG. 2. In one configuration, this data includes the dog's weight in kilograms, thorax girth in centimeters, and abdominal girth in centimeters.

Figure 5:
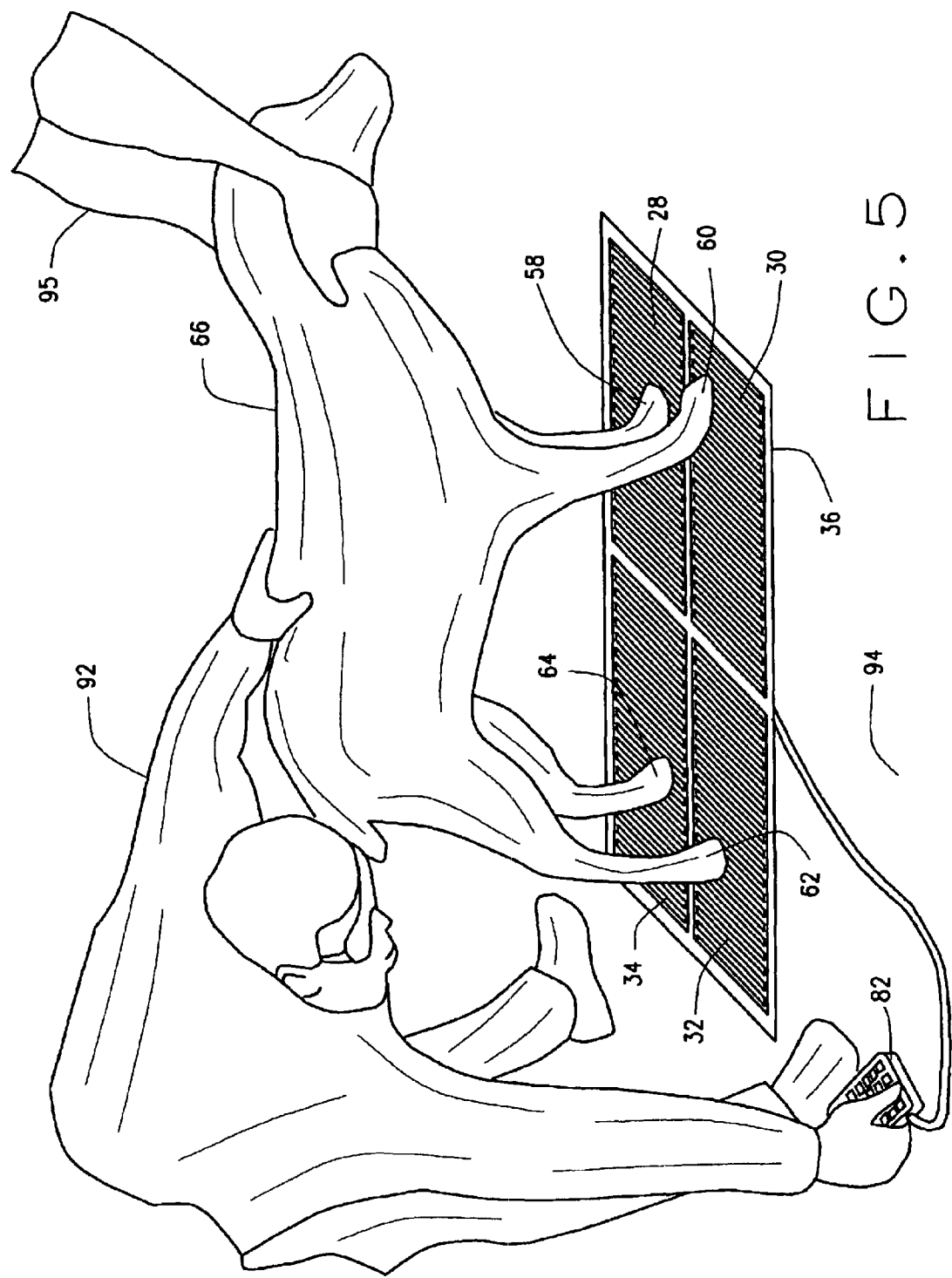
FIG. 5 is a pictorial view of a dog being positioned on the configuration of the present invention represented in FIG. 1.

Mat 36 is placed on a surface 94 as shown in FIG. 5. A raised table can be used, but for the safety of dog 66 being tested, surface 94 is preferably a floor rather than a raised table. One paw 58, 60, 62, 64 of dog is placed in contact with each of the four electrode pairs 28, 30, 32, and 34. Operator 92 and/or an assistant 95 ensures that dog 66 remains standing while being kept as still as possible for about 20 to 30 seconds, which is sufficient in one configuration of the present invention to perform the impedance measurements to be used in the regression equation. For a well-behaved dog 66, standing for 20 to 30 seconds should pose no problem. For less well-behaved dogs 66, it is permissible to calm the dog by touching the animal during the measurement, as long as all four paws 58, 60, 62, 64 remain on mat 36, one paw on each electrode pair 28, 30, 32, and 34. The accuracy of the measurement may suffer, however, if pad or mat 36 is touched by other conductive or reactive items, including a person's skin ("Reactive," in this sense, refers to electrical impedance). Thus even the though dog 66 can be touched, no one should touch electrode array mat 36 or any of the electrodes thereon while a measurements is in progress.

No further action is required on the part of operator 92, as processor 80 will operate the apparatus to perform the two-legged and four-legged impedance measurements automatically. After the measurements are performed, a regression equation such as that shown in FIG. 10 (or another one obtained experimentally) is used by the digital circuitry to determine the percentage of fat in the body of dog 66. This percentage is displayed on LCD display 26. In one configuration, a key or combination of keys on keypad 24 can be pressed to ready the apparatus for measuring another dog 66 without having to switch the apparatus off and on again.

More generally, the method for measuring body fat of the animal includes measuring a first electrical impedance between a front foot pad of the animal and a rear foot pad of the animal, measuring a second electrical impedance between two front foot pads of the animal in parallel with one another and two rear foot pads of the animal in parallel with one another, and utilizing the first electrical impedance, the second electrical impedance, and a regression relationship, determining the body fat of the animal. To measure the first impedance and the second impedance, the animal stands on an electrode array that contacts the foot pads of the animal. The array includes four pairs of interdigitated electrodes, and a different paw stands on each pair of interdigitated electrodes. Raw zoometric data is entered by the operator into a hand held controller in one configuration, and this data is used in addition to the impedance measurements to determine the body fat of the animal. The regression relationship illustrated in FIG. 10 is used in one configuration to determine the percentage of body fat of the dog, and the thorax resistance is determined utilizing a relationship written as $Z_{torso}=2(Z_4)-Z_2$, where $Z_{torso}$ is the complex torso impedance, $Z_4$ is the second measured impedance, $Z_2$ is the first measured impedance, and ThoraxResistance is the real part of $Z_{torso}$.

Errors can be caused if dog 66 lifts or moves any of its paws 58, 60, 62, or 64 during a measurement. This condition can be recognized by circuitry 16 because the impedance measurement will vary with the movement or lifting of any of the paws 58, 60, 62, or 64 being used for an impedance measurement. Thus, in one configuration, processor 80 is configured to display an error message on LCD display 26 when an error condition is recognized. In this case, another measurement can be made while ensuring that the paws of dog 66 remain still and in contact with the proper electrodes. In some cases, the pads of the dog's feet may be too thick to obtain an impedance measurement. In this case, the pads of the feet can be moistened by wiping with a damp cloth and the measurement repeated. In other cases, operator 92 may enter data that is clearly unreasonable or out of range (for example, the entered weight of the dog is outside the range of dogs used to determine the regression equation, is above the maximum weight expected for the largest dog that can fit on pad 36, or is negative). In this case, processor 80, in one configuration, uses display 26 to prompt operator 92 to enter the data again.

It will thus be understood that configurations of the present invention provide methods and apparatus for non-invasive diagnostic testing of animals for body fat, and are of particular use in estimating body fat in dogs. Configurations described above and variations thereof are practical for use in a veterinary office, and can be used by veterinarians for diagnosing obesity in pet animals, including dogs. The results are more accurate, objective, and more uniform than other methods commonly used by pet health professionals and do not require anesthetizing the animal or the use of X-rays. Although electrodes are used, there is no need to affix them to the animal. The animal merely needs to stand still on a mat while the measurement is taken, possibly after having its foot pads moistened. The voltage and current passing through the body of the animal is miniscule and harmless. In at least one configuration of the present invention, a few dimensions of the animal are taken with a ruler or tape measure, following which the animal merely stands still on a mat for about 20 or 30 seconds while the electrical measurements are taken and results displayed. No discomfort is experienced by the animal at any time, other than perhaps the general anxiety of being brought to a veterinary office for examination. Even that general anxiety, if present, can be relieved by the animal's owner, who can be allowed to comfort the animal by his or her touch even as the electrical measurements are taken.

As used in the appended claims, the use of the terms "first" and "second" to distinguish different measurements, electrodes, etc., are not intended to imply any ordering of importance or magnitude, or any temporal ordering, unless otherwise explicitly stated or necessarily required by implication. Furthermore, the use of the words "includes" or "having" is intended in the same sense as the word "comprise." Thus, unless explicitly indicated to the contrary, a first element that "includes" a second element is not restricted to including a single element of the second element, but may include multiple instances of the second element as well as additional elements that may or may not be specifically recited in the claim.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An apparatus for measuring at least one body composition measure of an animal, said apparatus comprising:
   a mat having four pairs of electrodes on a surface thereof, each said electrode pair configured to contact a different paw of an animal standing on the mat;
   electronic circuitry electrically coupled to the four pairs of electrodes and configured to utilize the four pairs of electrodes to measure a first impedance of the animal standing on the mat through one front paw of the animal and one rear paw of the animal and a second impedance of the animal standing on the mat though both front paws of the animal in parallel and both rear paws of the animal in parallel; and
   the electronic circuitry including a processor configured to determine a body composition measure of the animal utilizing the first measured impedance and the second measured impedance.

2. An apparatus in accordance with claim 1 wherein the animal for which the pairs of electrodes, electronic circuitry, and processor are configured is a dog.

3. An apparatus in accordance with claim 1 wherein the processor is configured to determine at least one member of the group consisting of body fat and body fat percentage of the animal utilizing an empirically determined regression relationship.

4. An apparatus in accordance with claim 3 wherein the processor is configured to determine body fat percentage.

5. An apparatus in accordance with claim 1 wherein the processor is configured to determine at least one body composition measure selected from the group consisting of total body water, fat free mass, lean body mass, and body fat of the animal.

6. An apparatus in accordance with claim 5 wherein the processor is configured to determine at least one body composition measure selected from the group consisting of total body water, fat free mass, lean body mass, and body fat of the animal, as a percentage of the weight of the animal.

7. An apparatus in accordance with claim 1 wherein the electronic circuitry comprises a current source coupled to a first electrode of each pair of electrodes, a voltmeter coupled to a second electrode of each pair of electrodes, and a controller operatively coupled to the current source to energize electrodes of selected pairs of electrodes to pass a current through one front paw of the animal and one rear paw of the animal for the first impedance measurement and though both front paws of the animal in parallel and both rear paws of the animal in parallel for taking the second impedance measurement; the voltmeter also coupled to the current source to determine the first impedance and the second impedance.

8. An apparatus in accordance with claim 7 wherein the voltmeter is a phase sensitive voltmeter and the current source is an alternating current source.

9. An apparatus in accordance with claim 1 further comprising a display coupled to the processor and a keypad coupled to the processor, and wherein the processor is configured to input zoometric data from the keypad and to use the zoometric data for determining the at least one body composition measure, and the processor is further configured to display the at least one body composition measure on the display.

10. An apparatus in accordance with claim 9 wherein the electronic circuitry, the display and the keypad are contained within a handheld unit electrically coupled to the pairs of electrodes on the mat via one or more flexible cables.

11. An apparatus in accordance with claim 9 wherein a portion of the electronic circuitry is contained within a handheld unit wirelessly coupled to another portion of the electronic circuitry that is wired to the pairs of electrodes on the mat.

12. An apparatus in accordance with claim 1 wherein each pair of electrodes is an interdigitated pair.

13. An apparatus in accordance with claim 12 wherein the mat comprises ABS plastic and the interdigitated pairs of electrodes comprise aluminum.

14. An apparatus in accordance with claim 12 wherein the mat is a flexible, non-conductive mat and the interdigitated pairs of electrodes comprise conductive paint.

15. A method for determining a relationship between body impedance of an animal and at least one body composition measure of an animal, said method comprising:

measuring a first electrical impedance between a front foot pad of the animal and a rear foot pad of the animal;

measuring a second electrical impedance between two front foot pads of the animal in parallel with one another and two rear foot pads of the animal in parallel with one another;

determining a torso impedance of the animal using the first measured impedance and the second measured impedance;

repeating said measuring of the first impedance, measuring of the second impedance, and determining the torso impedance for a plurality of animals of the same species;

obtaining an independent determination of the at least one body composition measure of the plurality of animals;

performing a regression analysis using the independent determination of the at least one body composition measure to determine a relationship between the at least one body composition measure and variables including torso impedance; and programming a processor to determine a body composition measure of an animal utilizing impedance measurements of an animal and the determined relationship.

16. A method in accordance with claim 15 wherein the animals are dogs.

17. A method in accordance with claim 15 wherein the at least one body composition measure is a body composition measure selected from the group consisting of body fat measure and body fat percentage.

18. A method in accordance with claim 15 wherein obtaining an independent determination of the at least one body composition measure of the plurality of animals comprises performing dual energy X-ray absorptiometry (DEXA) analysis.

19. A method in accordance with claim 15 wherein said measuring the first impedance and said measuring the second impedance each comprise measuring complex impedances.

20. A method in accordance with claim 15 further comprising measuring raw zoometric data for each animal, and said performing a regression analysis includes utilizing the measured raw zoometric data to determine a relationship between the at least one body composition measure and variables including torso impedance and the zoometric data.

21. A method for measuring at least one body composition measure of an animal, said method comprising:

standing the animal on a pad having an electrode array contacting foot pads of the animal, wherein the electrode array has four pairs of interdigitated electrodes and wherein a different paw of the animal is standing on each pair of interdigitated electrodes;

measuring a first electrical impedance between a front foot pad of the animal and a rear foot pad of the animal;

measuring a second electrical impedance between two front foot pads of the animal in parallel with one another and two rear foot pads of the animal in parallel with one another; and utilizing the first electrical impedance, the second electrical impedance, and a regression relationship to determine the at least one body composition measure of the animal.

22. A method in accordance with claim 21 further comprising moistening the foot pads of the animal.

23. A method in accordance with claim 21 wherein the animal is a dog.

24. A method in accordance with claim 21 wherein the at least one body composition measure is selected from the group consisting of total body water, fat free mass, lean body mass, and body fat of the animal.

25. A method in accordance with claim 21 wherein the at least one body composition measure is selected from the group consisting of total body water, fat free mass, lean body mass, and body fat of the animal, as a percentage of the weight of the animal.

26. A method in accordance with claim 21 wherein raw zoometric data of the animal is utilized in addition to the first electrical impedance, the second electrical impedance and the regression relationship to determine the at least one body composition measure of the animal.

27. A method in accordance with claim 21 further comprising entering raw zoometric data utilizing a hand-held controller and displaying the determined at least one body composition measure on a display of the hand-held controller.

28. A method in accordance with claim 21 wherein the animal is a dog, the at least one body composition measure comprises body fat percentage, and further wherein utilizing the first electrical impedance, the second electrical impedance, raw zoometric data of the animal and a regression relationship to determine the at least one body composition measure of the animal comprises determining body fat percentage as a percentage weight of the animal utilizing a relationship written as:

% Fat=−27.2−2.16×Weight+2.85×AbdomiralGirth+0.0326×ThoraxResistance−67.7×(AbdominalGirth/ThoraxGirth), wherein Weight is the weight of the animal in kilograms, AbdominalGirth is the abdominal girth of the animal in centimeters, ThoraxResistance is a resistance determined from the first measured impedance and the second measured impedance, and ThoraxGirth is the thorax girth of the animal measured in centimeters.

29. A method in accordance with claim 28 wherein ThoraxResistance is determined utilizing a relationship written as: $Z_{torso}=2(Z_4)-Z_2$, where $Z_{torso}$ is the complex torso impedance, $Z_4$ is the second measured impedance, $Z_2$ is the first measured impedance, and ThoraxResistance is the real part of $Z_{torso}$.

30. A method for measuring at least one body composition measure of an animal, said method comprising:

standing the animal on an electrode array contacting the foot pads of the animal;

measuring a first electrical impedance between a front foot pad of the animal and a rear foot pad of the animal;

measuring a second electrical impedance between two front foot pads of the animal in parallel with one another and two rear foot pads of the animal in parallel with one another; and utilizing the first electrical impedance, the second electrical impedance, and a regression relationship to determine the at least one body composition measure of the animal, wherein the animal is a dog.

31. A method in accordance with claim 30 wherein the at least one body composition measure comprises body fat percentage, and further wherein utilizing the first electrical impedance, the second electrical impedance, raw zoometric data of the animal and a regression relationship to determine the at least one body composition measure of the animal comprises determining body fat percentage as a percentage weight of the animal utilizing a relationship written as:

% Fat=−27.2−2.16×Weight+2.85×AbdominalGirth+0.0326×ThoraxResistance−67.7×(AbdominalGirth/ThoraxGirth), wherein Weight is the weight of the animal in kilograms, AbdominalGirth is the abdominal girth of the animal in centimeters, ThoraxResistance is a resistance determined from the first measured impedance and the second measured impedance, and ThoraxGirth is the thorax girth of the animal measured in centimeters.

32. A method in accordance with claim 31 wherein ThoraxResistance is determined utilizing a relationship written as: $Z_{torso}2(Z_4)-Z_2$, where $Z_{torso}$ is the complex torso impedance, $Z_4$ is the second measured impedance, $Z_2$ is the first measured impedance, and ThoraxResistance is the real part of $Z_{torso}$.

\* \* \* \* \*